United States Patent
Masumoto (10) Patent No.: US 10,347,033 B2
(45) Date of Patent: Jul. 9, 2019

(54) THREE-DIMENSIONAL IMAGE DISPLAY APPARATUS, METHOD, AND PROGRAM (71) Applicant: FUJIFILM Corporation, Tokyo (JP)

(72) Inventor: Jun Masumoto, Tokyo (JP)

(73) Assignee: FUJIFILM Corporation, Minato-Ku, Tokyo (JP)

(*) Notice: Subject to any disclaimer, the term of this patent is extended or adjusted under 35 U.S.C. 154(b) by 58 days.

(21) Appl. No.: 14/644,856

(22) Filed: Mar. 11, 2015

(65) Prior Publication Data
US 2015/0187119 A1    Jul. 2, 2015

Related U.S. Application Data (63) Continuation of application No. PCT/JP2013/005327, filed on Sep. 9, 2013.

(30) Foreign Application Priority Data

Sep. 13, 2012 (JP) .................. 2012-201083

(51) Int. Cl.
G06T 15/08 (2011.01)
A61B 6/00 (2006.01)
(Continued)

(52) U.S. Cl.
CPC ............ G06T 15/08 (2013.01); A61B 6/466 (2013.01); A61B 6/503 (2013.01); G06T 11/00 (2013.01);
(Continued)

(58) Field of Classification Search
None
See application file for complete search history.

(56) References Cited

U.S. PATENT DOCUMENTS 6,383,135 B1 * 5/2002 Chikovani ............ G06F 19/325
600/300
6,470,207 B1 * 10/2002 Simon .................... A61B 6/463
378/207
(Continued)

FOREIGN PATENT DOCUMENTS

JP    2001-195610 A    7/2001
JP    2004-174248 A    6/2004
(Continued)

OTHER PUBLICATIONS

N. Kawamura et al., "Examination of Bronchus Extraction Algorithm using Multi Slice CT Images", The Institute of Electronics, Information and Communication Engineers, Technical Report, MBE, ME and bio-cybernetics, 2005, pp. 11-14, vol. 105, No. 221.
(Continued)

Primary Examiner — Said Broome
(74) Attorney, Agent, or Firm — Sughrue Mion, PLLC (57) ABSTRACT A structure extraction unit extracts a heart region from a three-dimensional image of a chest, an image display control unit displays a volume rendering of the extracted heart region, an information adding unit adds additional information such as text and voice to a VR image displayed according to desired display conditions which include an image orientation. The display conditions when the additional information is added are stored with the additional information as designated display conditions. An allowable range setting unit sets a predetermined allowable range for the designated display conditions. During subsequent display of the VR image, an information reproducing unit enables the added information to be reproduced when display conditions are within the allowable range of the designated display conditions.

6 Claims, 7 Drawing Sheets (51) Int. Cl.
  *G06T 11/00* (2006.01)
  *G06T 19/00* (2011.01)
(52) U.S. Cl.
  CPC ............ *G06T 19/006* (2013.01); *A61B 6/463* (2013.01); *G06T 2207/10081* (2013.01); *G06T 2207/30048* (2013.01); *G06T 2207/30061* (2013.01); *G06T 2207/30101* (2013.01); *G06T 2210/41* (2013.01)

(56) References Cited

U.S. PATENT DOCUMENTS

| | | | |
|---|---|---|---|
| 2004/0101175 | A1 | 5/2004 | Yarger et al. |
| 2004/0233171 | A1* | 11/2004 | Bell .................... G06T 15/40 345/168 |
| 2010/0128963 | A1 | 5/2010 | Waku et al. |
| 2011/0166418 | A1 | 7/2011 | Aoyagi et al. |
| 2012/0136208 | A1 | 5/2012 | Itai |
| 2012/0139915 | A1 | 6/2012 | Muikaichi et al. |
| 2012/0182291 | A1* | 7/2012 | Rawat .................... G06T 17/00 345/419 |

FOREIGN PATENT DOCUMENTS

| | | |
|---|---|---|
| JP | 2010-148866 A | 7/2010 |
| JP | 2010-220742 A | 10/2010 |
| JP | 2011-139797 A | 7/2011 |
| JP | 2011-139821 A | 7/2011 |
| JP | 2011-206168 A | 10/2011 |
| JP | 2011-212314 A | 10/2011 |
| JP | 2012-075645 A | 4/2012 |
| JP | 2012-110549 A | 6/2012 |
| WO | 2011155118 A1 | 12/2011 |

OTHER PUBLICATIONS

J. Masumoto et al., "Automated Liver Segmentation Method for Dynamic CT Data Using Non-Rigid Registration", Journal of Computer Aided Diagnosis of Medical Images, Jun. 2003, pp. 29-38, vol. 7, No. 4-1.
P.S. Sulaiman et al., "A Liver Level Set (LLS) Algorithm for Extracting Liver's Volume Containing Disconnected Regions Automatically", IJCSNS International Journal of Computer Science and Network Security, Dec. 2008, pp. 246-252, vol. 8, No. 12.
T. Hitosugi et al., "Development of a liver extraction method using a level set method and its performance evaluation", Computer Aided Diagnosis of Medical Images, Jun. 2003, pp. 1-9, vol. 7, No. 4- 2.
M. Freiman et al., "Liver tumors segmentation from CTA images using voxels classification and affinity constraint propagation", Int J CARS, Jun. 24, 2010.
International Search Report of PCT/JP2013/005327 dated Nov. 12, 2013.
Communication dated Nov. 4, 2015, from the Japanese Patent Office in counterpart application No. 2012-201083.
Communication dated May 31, 2016, from the Japanese Patent Office in counterpart application No. 2012- 201083.
Communication dated Jul. 8, 2016, from the European Patent Office in counterpart European Application No. 13837821.1.

* cited by examiner

THREE-DIMENSIONAL IMAGE DISPLAY APPARATUS, METHOD, AND PROGRAM

CROSS-REFERENCE TO RELATED APPLICATIONS

This application is a Continuation of PCT International Application No. PCT/JP2013/005327 filed on Sep. 9, 2013, which claims priority under 35 U.S.C. § 119(a) to Japanese Patent Application No. 2012-201083 filed on Sep. 13, 2012. Each of the above applications is hereby expressly incorporated by reference, in its entirety, into the present application.

BACKGROUND OF THE INVENTION

Field of the Invention

The present invention relates to a three-dimensional display apparatus and method for displaying three dimensional images which are composed of a plurality of tomographic images obtained by tomographic imaging of an object, and also relates to a program for causing a computer to execute the three-dimensional image display method.

Description of the Related Art

In recent years, three-dimensional images of high quality are increasingly used for diagnostic imaging, accompanying advances in medical instruments (for example, multi-detector CT's, and the like). There are cases in which it takes time for a doctor to find and diagnose a desired observation portion because the three-dimensional images, which are composed of a large number of two-dimensional tomographic images, contain a large amount of information. Therefore, various types of techniques for improving visibility of the entirety of a structure and a lesion contained in the structure have been proposed. In such techniques, a structure of interest is identified, and a three-dimensional visualization image of the structure of interest is generated and displayed from a three-dimensional image containing the structure of interest. In such a case, a volume rendering (VR) display or a surface rendering (SR) display of the three dimensional image is performed by using a maximum intensity projection method, (MIP method), a minimum intensity projection method (MinIP method), and a ray summation (RaySum), for example.

The three-dimensional visualization images displayed by such techniques are of high definition, which enables the detailed shapes of very fine blood vessels and various organs to be visualized as they are. Accordingly, a doctor who is a user often makes a diagnosis by using a displayed three-dimensional visualization image and adds information such as comments, observations, or the like with respect to the blood vessels or organs identified by the three-dimensional visualization image to the image at the same time. In such a case, the doctor interactively changes display conditions by rotating, moving in parallel, and enlarging the three-dimensional visualization image, for example. When display conditions which are desirable for the observations and the like to be recorded are obtained, the doctor captures the three-dimensional visualization image and adds additional information such as the observations and the like to a captured still image.

In addition, various techniques have been proposed to display such three-dimensional images, to which the additional information has been added, together with the additional information. For example, in the technique proposed in Patent Document 1 (Japanese Unexamined Patent Publication No. 2001-195610), annotations and voxel data are made to correspond to each other in three-dimensional images in advance. When a cross section to be displayed is set, the distances between the cross section and positions to which the annotations are linked are computed. Then, in the case that the value of the distance is less than or equal to the threshold value, an annotation will be displayed. Further, Patent Document 2 (Japanese Unexamined Patent Publication No. 2011-139797) proposes a technique for indicating a marker when a viewpoint approaches the position of a tumor candidate in a virtual endoscopic image generated from a three-dimensional image. In addition, Patent Document 3 (Japanese Unexamined Patent Publication No. 2011-139821) proposes a technique for displaying an arrow which indicates the direction toward a lesion part. Moreover, Patent Document 4 (Japanese Unexamined Patent Publication No. 2011-206168) proposes a technique for when a doctor makes his observation by using three-dimensional images and examines a subject by utilizing an endoscope. The technique displays a label on which the doctor's observation is recorded in an endoscopic image being displayed when the endoscope approaches the position to which the observation is added.

SUMMARY OF THE INVENTION

A captured three-dimensional visualization image related to a three-dimensional image, to which additional information has been added, is to be displayed later so that a final judgment regarding diagnosis will be made. In such a case, if a doctor who has added additional information to the image is the same as a doctor who makes a final judgment, it is possible to understand from which position and which tissue or blood vessel the captured image was captured to observe. However, if a different doctor makes a final judgment, it is often the case that the intention of the doctor, who has added the information, cannot be understood by the different doctor. In this case, the different doctor can understand the intention with which the image has been captured based on the contents of the observations included in the additional information.

However, although the orientation of the captured image may be considered to be easily viewed by the doctor, who has captured the image, there are cases in which another doctor different from the doctor who has captured the image desires to slightly change the orientation of the captured image. Further, when displaying the three-dimensional visualization image while interactively changing display conditions, there are cases in which a plurality of captured images are created for the three-dimensional visualization. In such a case, displaying all the information which has been added to the captured images will interfere with observation of the three-dimensional visualization image. Moreover, it will not be possible to understand which information and which display conditions are matched together.

Further, the technique disclosed in Patent Document 1 described above displays the additional information when displaying a cross section. This technique cannot be applied in the case that display conditions are interactively changed. Further, the techniques disclosed in Patent Documents 2 through 4 display additional information when approaching the position to which the additional information is added. In such techniques, there is a possibility that the meaning of displayed additional information cannot be understood if the orientation of a three-dimensional visualization image at the time that the additional information was added to the image differs from the orientation of the three-dimensional visualization image at the time that the additional information is displayed.

The present invention has been developed in view of the foregoing circumstance. It is an object of the present invention to facilitate viewing necessary information when information added to a three-dimensional image is displayed.

A three-dimensional image display apparatus according to the present invention includes:

an image display control means that three-dimensionally visualizes a three-dimensional image of an object and displays a three-dimensional visualization image on display means;

a display condition setting means that sets display conditions including an orientation in which the three-dimensional visualization image is displayed;

a storage means that correlates and stores designated display conditions and additional information, the designated display conditions being designated to add the additional information regarding the three-dimensional visualization image;

an allowable range setting means that sets an allowable range for the designated display conditions; and an information reproducing means that determines whether display conditions are within the allowable range of the designated display conditions when displaying the three-dimensional visualization image while changing the display conditions and that enables the additional information correlated with the designated display conditions to be reproduced when an affirmative determination is made.

The additional information may be information which is automatically obtained by analyzing the three-dimensional visualization image, in addition to information which is obtained by a user who observed a three-dimensional visualization image through the user's observation of the three-dimensional visualization image. Examples of the information may include text such as observations and the like, annotations such as an arrow and the like, objects of arbitrary shapes, audio data and the like.

The expression "enables the additional information to be reproduced" includes displaying information which indicates that additional information is present, in addition to displaying or reproducing the additional information itself. The information which indicates that additional information is present refers to information that causes the additional information to be displayed or reproduced when the information is designated. It is preferable for such information, which indicates that additional information is present, to be displayed and for audio data to be reproduced by designating the displayed information, particularly when the additional information is the audio data. This is because, if the additional information is to be reproduced as soon as the display conditions fall within the allowable range of the designated display conditions, audio will be suddenly reproduced while the three-dimensional visualization image is being displayed.

Note that in the three-dimensional display apparatus according to the present invention, the image display control means may be means which changes the display conditions of the three-dimensional visualization image to the designated display conditions when the additional information is enabled to be reproduced.

Further, in the three dimensional image display apparatus according to the present invention, the information reproducing means may be means which displays or reproduces the additional information.

Further, in the three dimensional image display apparatus according to the present invention, the information reproducing means may be means which displays information for displaying or reproducing the additional information.

Further, in the three dimensional image display apparatus according to the present invention, the display condition setting means may be means which sets at least one of a display position, an enlargement ratio, and image quality of the three-dimensional visualization image in addition to the orientation, as display conditions.

Further, in the three dimensional image display apparatus according to the present invention, the display condition setting means may be means which sets at least the orientation and the display position as display conditions when the three-dimensional image is a virtual endoscopic image.

A three-dimensional image display method according to the present invention includes the steps of:

three-dimensionally visualizing a three-dimensional image of an object and displaying a three-dimensional visualization image on display means;

setting display conditions including an orientation in which the three-dimensional visualization image is displayed;

setting an allowable range for the designated display conditions designated to add additional information regarding the three-dimensional visualization image;

determining whether display conditions are within the allowable range of the designated display conditions when displaying the three-dimensional visualization image while changing the display conditions; and enabling the additional information regarding the three-dimensional visualization image to be reproduced when an affirmative determination is made, the additional information being that correlated with the designated display conditions.

Note that the three-dimensional image display method according to the present invention may be provided as a program which causes a computer to execute.

According to the present invention, the allowable ranges are set for the designated display conditions including the orientation. For displaying three-dimensional visualization image while changing the display conditions, if the display conditions fall within the allowable ranges of the designated display conditions, additional information correlated with the designated display conditions will be enabled to be reproduced. That is, if the display conditions approach the display conditions, at which the additional information regarding the three-dimensional visualization image has been added, the additional information will be reproduced. Therefore, only necessary additional information will be displayed even when a user different from the user who has added the additional information displays the three-dimensional visualization image while changing the display conditions. As a result, unnecessary additional information will not interfere with an observation of the three-dimensional visualization image. Further, it can be easily understood from the reproduced additional information which orientation the three-dimensional image has been viewed with, and thereby viewing and understanding the orientation and the additional information of the three-dimensional visualization image as a whole are facilitated.

DETAILED DESCRIPTION OF THE PREFERRED EMBODIMENTS

Figure 1:
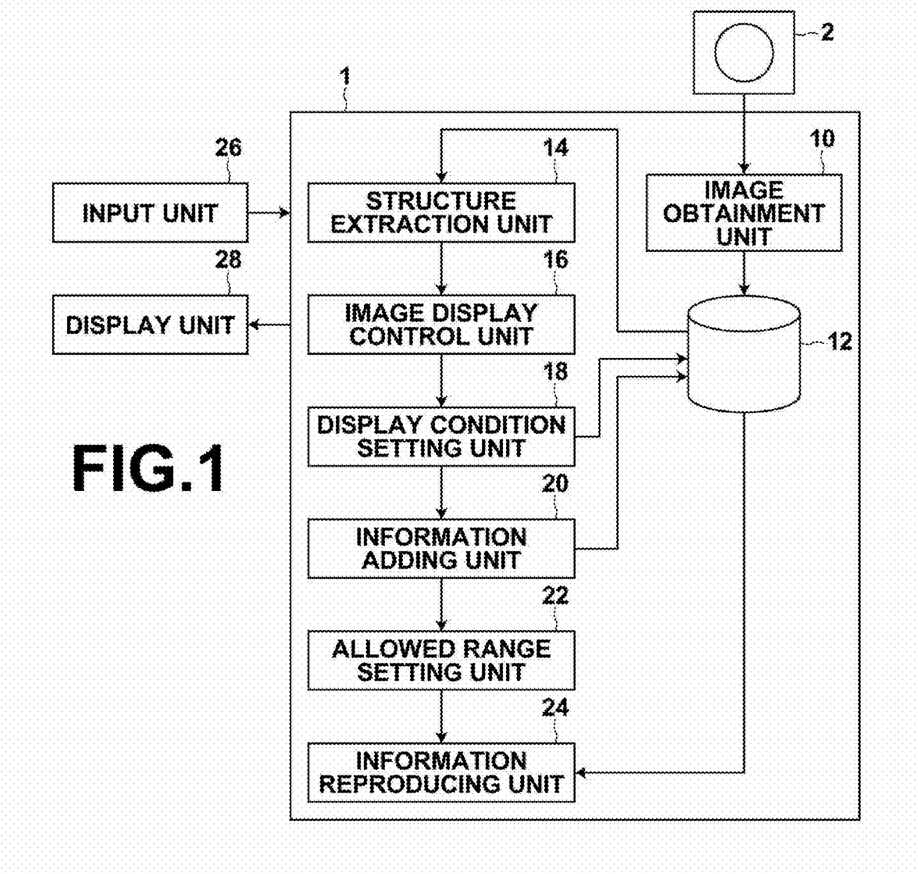
FIG. 1 is a block diagram that schematically illustrates the configuration of a three-dimensional image display apparatus of an embodiment of the present invention.

Hereinafter, the embodiment of the present invention will be described with reference to the drawings. FIG. 1 is a block diagram that schematically illustrates the configuration of a three-dimensional image display apparatus of an embodiment of the present invention. Note that the configuration of a three-dimensional image display apparatus 1 illustrated in FIG. 1 is realized by causing a three-dimensional image display program read into an auxiliary storage device to execute on a computer. This program is recorded in recording media such as CD-ROM's and the like or is distributed via a network such as the Internet to be installed in computers.

The three-dimensional image display apparatus 1 according to the present embodiment includes an image obtainment unit 10, a storage unit 12, a structure extraction unit 14, an image display control section 16, a display condition setting unit 18, an information adding unit 20, an allowable range setting unit 22, an information reproducing unit 24, an input unit 26, and a display unit 28.

The image obtainment unit 10 functions as a communication interface which obtains a three-dimensional image V0 acquired by imaging a chest of a subject in a modality 2 such as multi-slice CT apparatuses, MRI apparatuses, or the like. Note that the modality 2 is a multi-slice apparatus in this embodiment. Further, the three-dimensional image group V0 is delivered via a LAN from the modality 2.

Here, the three-dimensional image V0 is obtained by laminating two-dimensional tomographic images which are sequentially obtained along the direction perpendicular to the tomographic sections of the chest which is a target for diagnosis. In the present embodiment, the three-dimensional image V0 is generated by overlapping a plurality of tomographic images acquired by the modality 2. Note that a three-dimensional image which has been obtained by using the CT apparatus is data in which the amount of X-ray absorption is stored for each voxel (i.e., a pixel position) that constitutes lattice points in a three-dimensional space. In the data, one signal value (when the CT apparatus is applied for imaging, the value represents the amount of the X-ray absorption.) is provided for each pixel position.

Note that the three-dimensional image V0 is added to with supplemental information specified by the DICOM (Digital Imaging and Communications in Medicine) specification. For examples, the supplemental information may include an image ID for identifying a three-dimensional image, a patient ID for identifying a subject, an examination ID for identifying an examination, a unique ID (UID) assigned to each piece of image information, the examination date on which the image information has been generated, the examination time, the kind of a modality which has been used in the examination to obtain the image information, information regarding the patient such as the name of the patient, age, gender, and the like, a site to be examined (a site to be imaged, a chest in the present embodiment), imaging conditions (whether contrast agent is used or not, the amount of radiation, and the like), a series number or an obtainment number when a plurality of images has been obtained for one examination.

The storage unit 12 is a large capacity storage device such as a hard disk and stores three-dimensional images V0 therein. In addition, the storage unit 12 also stores capture images, display conditions, and additional information to be described below.

The structure extraction unit 14 extracts a heart from a three-dimensional image V0 of a chest as a structure. In particular, the structure extraction unit 14 estimates the range of a signal value (CT value), in which the heart is present in the three-dimensional image V0, and extracts the heart by carrying out a threshold processing using the value of the range.

The image display control unit 16 displays a volume rendering (VR) image of the three-dimensional image V0 by using a volume rendering method. In particular, the image display control unit 16 emits a virtual light beam from a projection plane toward the three-dimensional image V0 and generates a three-dimensional image by virtual reflected light from the interior of the object, based on the colors (R, G, B) and opacity corresponding to the respective signal values in the three-dimensional image V0. Then, the image display control unit 16 further generates a projection image, which enables seeing through a three-dimensional structure in the interior of the object, on the projection plane from the three-dimensional image and displays this projection image as a volume rendering image (VR image) on the display unit 28. In this case, the VR image corresponds to the three-dimensional visualization image of the present invention. Note that the colors and opacity are defined in a predetermined color template, and the signal values of the respective pixel positions in the three-dimensional image V0 are converted into pixel values of the projection image, i.e., the VR image, based on the colors and opacity set according to the predetermined color template by the alpha blending method. In the present embodiment, a heart is first extracted, and then a volume rendering image thereof is displayed. Therefore, a color template, in which structures other than the extracted heart in the three-dimensional image of the chest has opacity of 0, is applied for displaying a VR image of the three-dimensional image.

The display condition setting unit 18 changes display conditions that include the orientation of the VR image, in response to instructions from an input unit 26 and outputs the instructions to the image display control unit 16. The display conditions refer to conditions for changing the orientation, the position on the projection plane, the enlargement ratio, and the image quality of a displayed VR image. The condition for changing the orientations applies a 3×3 rotation matrix. The rotation matrix represents a rotation angle with respect to the respective x, y, z axes based on the orientation in which the VR image is viewed from the front, for example. The condition for changing the position represents the two-dimensional moving directions on the projection plane, e.g., the amount of changes of coordinate values in x direction and y direction on the projection plane, from a state in which the heart is displayed at the reference position in the VR image. The condition for changing enlargement ratio represents the enlargement ratio itself, which is the amount of changes in the size from a state in which the heart is displayed with the reference size on the VR image. The condition for changing the image quality is the color template used for displaying the VR image. Note that when the three-dimensional image is displayed as a monochrome image by the MIP method, the MinIP method, and the like, the condition for the changing the image quality is a window level value (WL value).

The display condition setting unit 18 receives instructions to change the display condition from the input unit 26, and outputs the changed display condition to the image display control unit 16. The image display control unit 16 changes the orientation of the projection plane of the three-dimensional image V0, the position of the projection plane, the distance between the three-dimensional image V0 and the projection plane, and signal values of the respective pixels of the three-dimensional image V0 and display the VR image on the display unit 28 so as to satisfy the changed display condition. This enables the VR image to be displayed by interactively changing the display conditions.

In such a manner, a doctor, i.e., a user, interactively changes the display conditions while displaying the VR image, and finds a display condition with which the doctor desires to input observations and the like. The image display control unit 16 receives the doctor's instructions to capture the image from the input unit 26 accordingly, and then captures the VR image being displayed with the desired display condition. Then, the image display control unit 16 generates a captured image and displays the capture image on the display unit 26.

The information adding unit 20 adds additional information to the captured image in response to the user's input from the input unit 26. Examples of the additional information include observations representing positions and levels of plaque or calcification in coronary artery, annotations such as arrows and the like, or observations by voice. Further, an object of an arbitrary shape for enclosing suspicious lesion sites may be included as the additional information. In this case, the additional information may be added to pixel positions of a three-dimensional image V0 by being associated therewith, which correspond to the respective pixel positions of a captured image, or may be added to the pixel position of the captured image by being associated therewith. In such a case, when the additional information is added to each of the pixel positions as a label, each of the pixel positions should be a position of the tip of a leader line or a position of the tip of an arrow of a label. Further, the additional information may be displayed as a list in a predetermined position (for example, a lower right position) of a display region in the captured image. Note that the additional information is not limited to the information input by a user, but may be information which has been automatically obtained by analyzing the three-dimensional image V0.

The input additional information is associated with the captured image and the display conditions (hereinafter referred to as designated display conditions) designated when the captured image was obtained and stored in the storage unit 12. Storing the additional information and the display conditions may be performed in response to the user's instructions from the input unit 26, or may be performed when the display conditions are changed by the predetermined amount or more from the state in which the captured image was displayed. In particular, changes in display conditions will be detected when the rotation angle becomes more than or equal to 5 degrees regarding the orientation, the amount of parallel movement becomes more than or equal to 20 mm regarding the position, or a change of the enlargement ratio becomes more than or equal to ±20%. Then, the additional information and the designated display conditions may be stored accordingly. Note that the designated display conditions to be stored at this time are not the display conditions which have been changed, but are the display conditions for when the additional information was added. In addition, as it is difficult to detect changes of color templates, it is not necessary to utilize the color templates to detect the changes in the display conditions.

The user repeats capturing an image (i.e., generating a captured image) from a three-dimensional image V0 and adding additional information thereto by repeating the aforementioned steps, and then a plurality of display conditions and multiple pieces of additional information are stored in the storage unit 12, respectively correlated to each other. Note that the plurality of designated display conditions and multiple pieces of additional information are also associated with the three-dimensional image V0 together with a plurality of captured images.

The allowable range setting unit 22 sets an arrowed range for designated displayed conditions which has been designated when additional information was added. The allowable range is a range of the display conditions with the designated display conditions as the reference such that the additional information correlated with the designated display conditions will be reproduced when the VR image approaches the designated display conditions. The allowable range includes at least one allowable range of the orientation, the position, and the enlargement ratio with the designated display conditions as the reference. In the present embodiment, allowable ranges should be set for all of the orientation, the position, and the enlargement ratio. For example, ±5 degrees for the orientation, ±20 mm for the position, and ±20% for the enlargement ratio are applied for the respective allowable ranges. Note that as it is difficult to set the allowable range of the color template, it is not necessary to set the allowable range thereof.

The information reproducing unit 24 enables the additional information correlated with the designated display conditions to be reproduced when the display conditions fall within the range of the designated display conditions, during display of the VR image while interactively changing the display conditions in a manner to be described later.

The input unit 26 includes a known input device such as a keyboard, a mouse, and the like.

The display unit 28 includes a known display device such as a liquid crystal, CRT, and the like.

Figure 2:
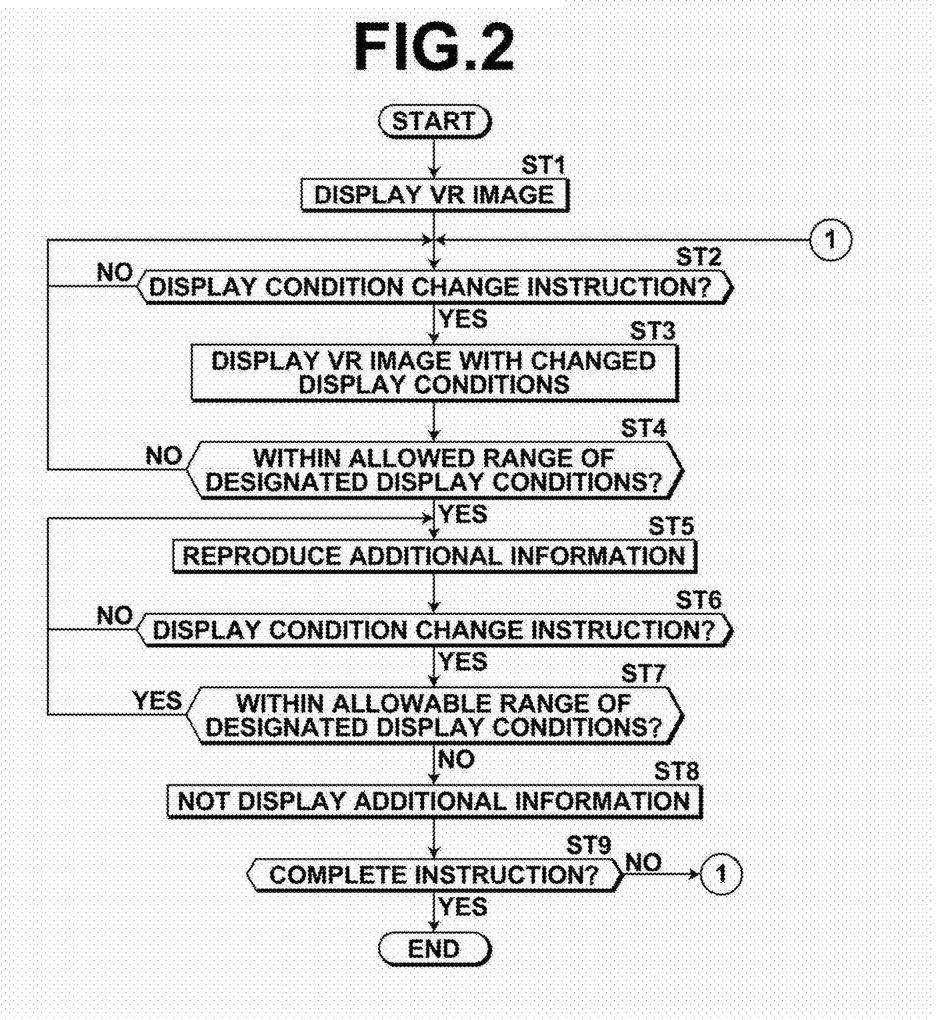
FIG. 2 is a flow chart that illustrates the process carried out in the present embodiment.

Next, a process carried out in the present embodiment will be described. FIG. 2 is a flow chart that illustrates the process carried out in the present embodiment. Note that the three-dimensional image V0 should be stored in the storage unit 12 by being associated with the respective captured images, a plurality of designated display conditions, and plural pieces of additional information, as described above. In the process, a VR image is displayed with reference display conditions at first, with respect to which instructions to change the display conditions will be received. A user operates the input unit 26 to make instructions to display the VR image. This causes the image display control unit 16 to display the VR image on the display unit 28 (step ST1).

Figure 3:
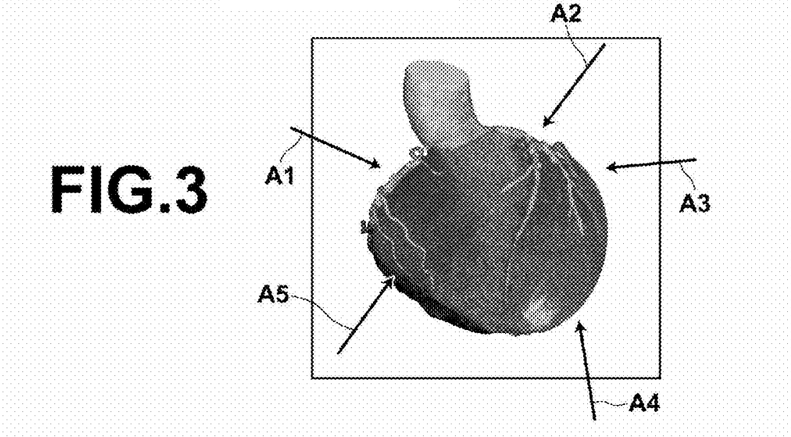
FIG. 3 is a diagram that illustrates a displayed VR image.

FIG. 3 is a diagram that illustrates a displayed VR image. The VR image shows a projection image of a heart with arrows directing directions, which are included in the designated display conditions, as illustrated in FIG. 3. Note that FIG. 3 shows five arrows A1 through A5. These arrows represent that pieces of additional information have been added to captured images, captured when viewing the VR image from the directions of the respective arrows. If the user makes instructions to change the display conditions from the input unit 26 (step ST2 affirmation), the display condition setting unit 18 and the image display control unit 16 will display the VR image with changed display conditions (step ST3). This enables the user to display the VR image with a desired orientation, position, enlargement ratio, and image quality.

Then, the information reproducing unit 24 determines whether the changed display conditions are within the allowable range of the designated display conditions (step ST4). If a negative determination is made in step ST4, the operation will return to step ST2 and the steps after step ST2 will be repeated. If an affirmative determination is made in step ST4, the information reproducing unit 24 will reproduce the additional information (step ST5). In this case, when the image quality of the display conditions (i.e., a color template) differs from that of the designated display conditions, the color template of the designated display conditions may be used to obtain the same image quality. Further in this case, an inquiry about whether to change the color template may be made to the user by displaying buttons for changing the color template, or the like. Then, only when the user's instructions to change the color template are made, the color template may be changed. Further, in addition to the color template, the display conditions for at least one of the orientation, the position, and the enlargement ratio of the VR image may be changed to the designated display conditions so that the VR image can be viewed in the same manner as when the additional image was added. This is because the display conditions for when the additional information are reproduced are close to the designated display conditions.

Figure 4:
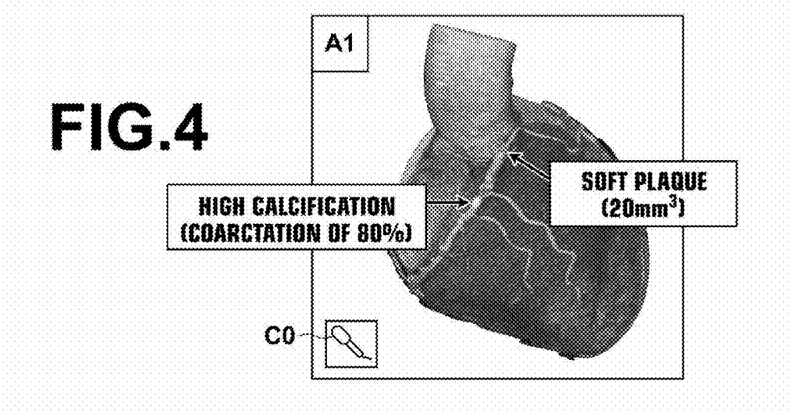
FIG. 4 is a diagram that illustrates a state in which additional information is reproduced.
Figure 5:
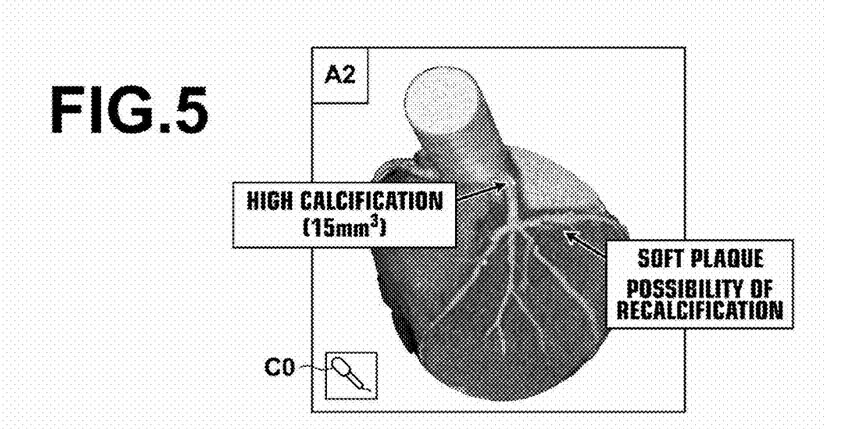
FIG. 5 is a diagram that illustrates a state in which additional information is reproduced.

Each of FIG. 4 and FIG. 5 is a diagram that illustrating a state in which the additional information is reproduced. Note that FIG. 4 illustrates a state in which additional information is reproduced when the display conditions fall within the allowable range of the designated display conditions corresponding to the arrow A1 in FIG. 3, whereas FIG. 5 illustrates a state in which additional information is reproduced when the display conditions fall within the allowable range of the designated display conditions corresponding to the arrow A2 in FIG. 3. As illustrated in FIG. 4, when the display conditions fall within the allowable range of the designated display conditions corresponding to the arrow A1, labels, on which observations such as "high degree of calcification (coarctation of 80%)" and "soft plaque (20 $mm^3$)" are described, are displayed, an icon C0 of a mark of a microphone, which represents that audio data is added, are displayed. Further, as illustrated in FIG. 5, when the display conditions fall within the allowable range of the designated display conditions corresponding to the arrow A2, labels, on which observations such as "high degree of calcification (15 $mm^3$)" and "soft plaque possibility of recalcification" are described, are displayed, an icon C0 of a mark of a microphone, which represents that audio data is added, are displayed. Note that the audio data can be reproduced by the user clicking the icon C0. Further, note that the audio data may be reproduced as soon as the display conditions fall within the allowable range of the designated display conditions, instead of displaying the icon C0. In addition, it is preferable for the labels to be displayed in the range that radially expands with the center of the display screen as the reference.

Figure 6:
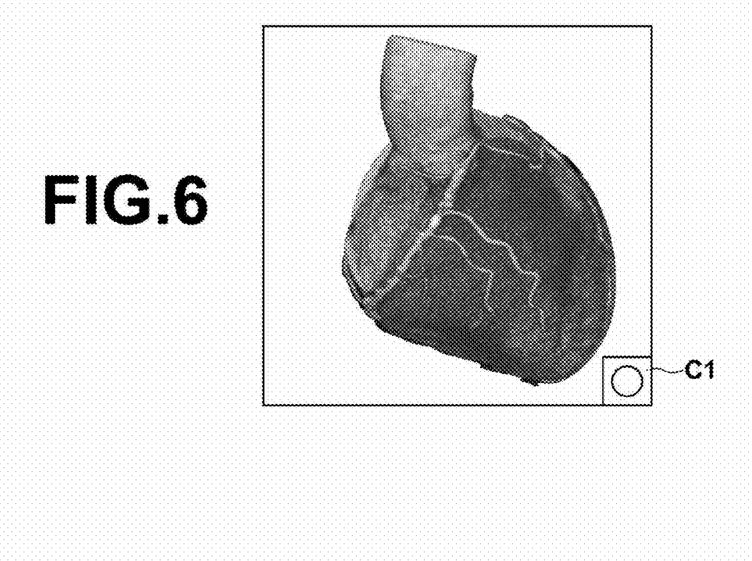
FIG. 6 is a diagram that illustrates a state in which additional information is reproduced.

Note that as illustrated in FIG. 6, an icon C1, which represents that the additional information is present, may be displayed instead of the additional information. In this case, the additional information can be reproduced by the user clicking the icon C1, as described regarding FIGS. 4 and 5.

Figure 7:
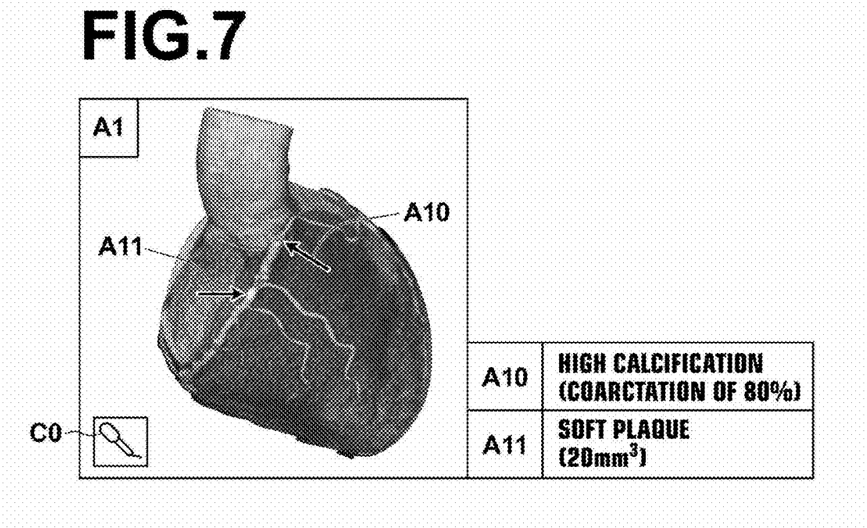
FIG. 7 is a diagram that illustrates a state in which additional information is reproduced.

Further, as illustrated in FIG. 7, only the arrows A10 and A11 indicating portions to which the additional information added may be displayed while a list of the additional information itself is displayed on the right side of the display screen. Further, the additional information may be switchable between the display and non-display in response to instructions from the input unit 26.

In such a state, whether instructions to change the display conditions are made is determined (step ST6). If a negative determination is made in step ST6, the operation returns to step ST5. If an affirmative determination is made in step ST6, whether the display conditions are within the allowable range of the designated display conditions is determined (step ST7). If an affirmative determination is made in step ST7, the operation returns to step ST5. If a negative determination is made in step ST7, the additional information will not be displayed (step ST8). Following step ST8, whether the instructions to complete the process were made is determined (step ST9). If a negative determination is made in step ST9, the operation returns to step ST2. If an affirmative determination is made in step ST9, the process is completed.

As described above, in the present embodiment, an allowable range is set for each of the designated display conditions, and when the display conditions fall within the allowable range of the designated display conditions, the additional information correlated with the designated display conditions can be reproduced during display of the VR image while changing the display conditions. Therefore, only the necessary additional information will be displayed when a user different from the user who has added the additional information displays the VR image while changing the display conditions. As the result, unnecessary additional information will not interfere with an observation of the VR image. Further, it can be easily understood from the reproduced additional information which orientation the VR image has been viewed with, and thereby viewing and understanding the orientation and the additional information of the VR image as a whole are facilitated.

Note that the process to be carried out for when a three-dimensional image V0 is displayed by volume rendering was described in the embodiment above. However, the present invention can be applied for when the three-dimensional image V0 is displayed by other displaying method such as MIP method, MinIP method, RaySum method, and the like. Further, in the case that the additional information was added to the VR image displayed by VR method, the additional information will be reproducible when the display conditions fall within the allowable range of each of the designated display conditions corresponding to those of the VR image. This may apply to cases that the three-dimensional image V0 is displayed by another displaying method, such as the MIP method, and the like, other than the VR display method.

Here, in the case that the number of the structures displayed as the VR image is small, the number of pieces of the additional information is also small. Accordingly, all pieces of the additional information can be reproduced without any problems when the display conditions fall within the allowable range of each of the designated display conditions. However, when the additional information is added not only to one structure but to various kinds of structures, which are targets contained over a wide range in the three-dimensional image V0, such as a chest or a chest and belly part of a human body including a plurality of structures, there is a possibility that all pieces of the additional information cannot be displayed when the display conditions fall within the range of each of the designated display conditions. Further, in the case that all pieces of the additional information are displayed, even if the additional information added to the structures in the interior of the organs is displayed in a state in which only the appearance of organs can be viewed but the interior of the organs cannot be viewed, it is impossible to understand to which structure each of the additional information is added. Therefore, there is no point in displaying the additional information in such a case.

Figure 8:
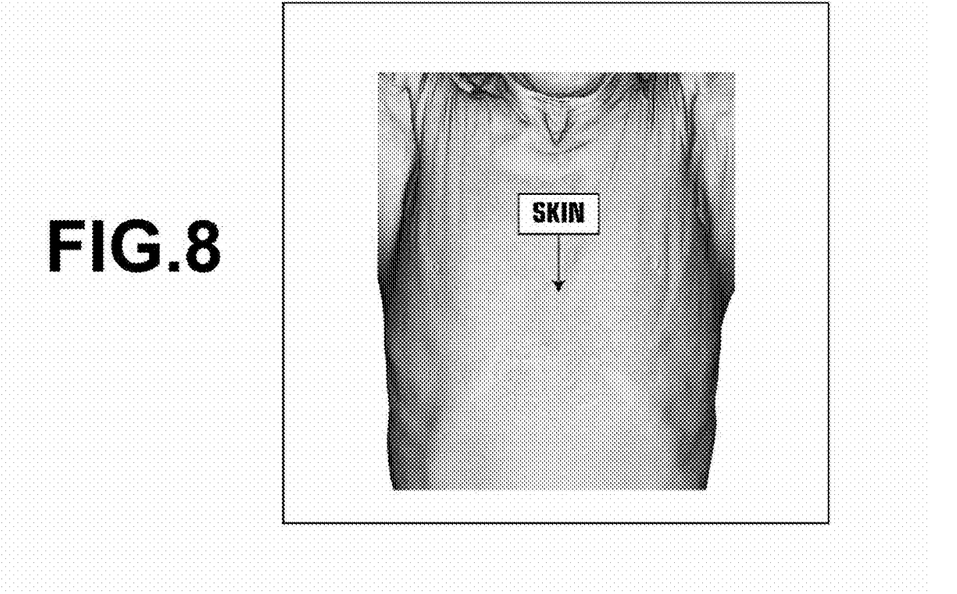
FIG. 8 is a diagram that illustrates a state in which body surface is displayed by VR.
Figure 9:
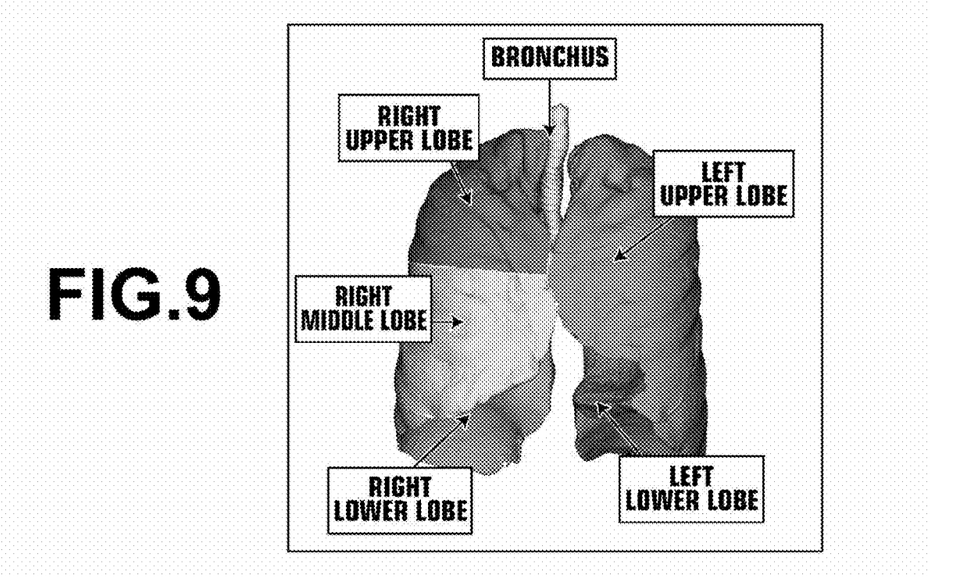
FIG. 9 is a diagram that illustrates a state in which opacity in the body surface is changed in the VR image shown in FIG. 8.

Accordingly, the additional information to be reproduced may be selected, based on the opacity of the three-dimensional image V0 to be displayed as the VR image. For example, when displaying the three-dimensional image V0 of the chest as the VR image, the opacity is being changed from the body surface toward the interior such that the structure of the interior of the chest is gradually displayed. In such a case, only the additional information of the opacity 1, in which that the additional information has been added to the structure, the surface of which can be viewed, among the structures which are displayed by VR display method may be reproduced. In more particular, In the case that only the body surface is displayed as the VR image, as shown in FIG. 8, only the additional information (the text "skin" in FIG. 8) which has been added in the state that the body surface will be displayed when the display conditions fall within the allowable range of the designated display conditions. Further, from the state illustrated in FIG. 8, the opacity of the body surface is gradually decreased and a VR image generated by projecting a lung region and bronchus onto a projection surface is displayed. In such a case, when the display condition fall within the allowable range of the designated display conditions, only the additional information (the texts "right upper lobe", "bronchus", and the like in FIG. 9), which has been added in a state in which the lung region and bronchus are displayed, will be reproduced.

Thereby, a large numbers of pieces of the additional information will not be displayed simultaneously, which enables the reproduced additional information to be easily viewed.

Further, in the aforementioned embodiment, the lung region and bronchus are extracted and the additional information may be added to these extracted parts when displayed with the designated display conditions. Moreover, the present invention can be applied to the case that the VR image of the three-dimensional image V0 of the belly part is displayed as well. For example, a target in the belly part is designated as a liver region. The liver region, hepatic artery, hepatic vein, portal vein, and neoplasm are extracted from the three-dimensional image V0, and the additional information is added to each of the liver region, hepatic artery, hepatic vein, portal vein, and neoplasm when each being displayed with the designated display conditions. Further, at the time of displaying the VR image, each piece of the additional information may be reproduced when the display conditions respectively fall within the allowable range of the designated conditions.

Here, a method for extracting the lung region, in which air is present in the lung field, may apply an arbitrary method such as a method in which a histogram of a signal value of each pixel position in the three-dimensional image V0 is generated and the lung region is subjected to the threshold processing, a region expanding method which is based on seed points that represent the lung region, and the like.

A method for extracting the bronchus may be a method in which an assembly of pixels within the bronchus region is extracted by the region expanding method, and thinning processing is conducted on the extracted bronchus region. Further, in such a method, the respective pixels on thin lines are classified into end points, edges (sides), and branch points based on the connecting relationship of the thin lines that represents the obtained bronchus so that tree-structure data which represents the bronchus is obtained. Further, as described in N. Kawamura et al., "Examination of Bronchus Extraction Algorithm using Multi Slice CT Images", THE INSTITUTE OF ELECTRONICS, INFORMATION AND COMMUNICATION ENGINEERS, Technical Report, MBE, ME and bio-cybernetics, Vol. 105, No. 221, pp. 11-14, 2005, and the like, a method for automatically extracting the bronchus may be applied.

Further, a method for extracting the liver region may apply a method in which the range of CT values where the liver is present in the three-dimensional image V0 is estimated, the threshold processing is conducted by using the value of the range, and a morphology filter is applied to the extracted region. As described in J. Masumoto et al., "Automated Liver Segmentation Method for Dynamic CT Data Using Non-Rigid Registration", Journal of Computer Aided Diagnosis of Medical Images", Vol. 7, No. 4-1, pp. 29-38, 2003, a method in which contrast patterns of the liver region are detected by utilizing a plurality of phase images of the liver taken in chronological order and the liver region is detected by using the detected contrast patterns is also applied. Further, level set methods as described in P. S. Sulaiman et al., "A Liver Level Set (LLS) Algorithm for Extracting Liver's Volume Containing Disconnected Regions Automatically", IJCSNS International Journal of Computer Science and Network Security, Vol. 8, No. 12, pp. 246-252, 2008 and T. Hitosugi et al., "Development of a liver extraction method using a level set method and its performance evaluation", Computer Aided Diagnosis of Medical Images, Vol. 7, No. 4-2, pp. 1-9, 2003 can be applied. Note that the method for extracting the liver region of the present invention is not limited to these methods, but an arbitrary method may be applied.

Further, as a method for extracting a hepatic artery, a hepatic vein, and a portal vein (hereinafter, there are cases that these are referred to simply as blood vessels), a method in which a main axis direction and the positional information regarding a plurality of candidate points that represent a target tissue composed by a linear structure are calculated and the plurality of the candidate points are reconstructed to be connected with each other by using a cost function which is a variable based on the calculated positional information and main axis direction, as disclosed in Japanese Unexamined Patent Publication No. 2010-220742, for example may be applied. Further, a method for automatically discriminating blood vessels from each other and extracting them as disclosed in Japanese Unexamined Patent Publication No. 2011-212314 may also be applied.

Further, a method for extracting blood vessels may apply a method in which a tree-structure is generated by connecting the respective nodes with each other from a first root node corresponding to a first tree-structure root node and a second root node corresponding to a second tree-structure root node based on the characteristics of the blood vessels which repeatedly branch from an origin of each of a first and a second linear structures and extends in directions away from the origin in such a manner to become wider. In this method, a cost function is used such that a cost which represents ease of connection with respect to a plurality of edges, each of which is capable of connecting with each node, and which bind a plurality of nodes together is weighted for each node. Further, in this method, the first and second linear structures are designated as the hepatic artery and the hepatic vein, respectively so that the hepatic artery and the hepatic vein can be discriminated and extracted. Further, in this method, the first and second linear structures are designated as the portal vein and hepatic artery, and the hepatic vein, respectively so that the portal vein and hepatic artery, and the hepatic vein can be discriminated and extracted. Note that in this method, the origin may be identified by an arbitrary method, and the root node corresponding to the origin may be identified by a well-known method based on the origin. For example, the origin may be designated on a displayed image by an input device such as a mouse, or the like. Alternatively, an origin detection unit may be applied for detecting an origin. The origin detection unit detects the origin by mechanically learning a plurality of teacher data, which represents that the origin is a known predetermined structure. Note that various known methods for extracting a root node by mechanically learning teacher data may be applied. For example, the Adaboost method can detect an origin based on the amount of characteristics of a known origin in teacher data.

Further, a tumor can be extracted by methods that utilize the Voxel Classification described in M. Freiman et al., "Liver tumors segmentation from CTA images using voxels classification and affinity constraint propagation", Int J CARS, 2010. Note that methods for extracting hepatic arteries, hepatic veins, portal veins, and tumors are not limited to these methods, but an arbitrary method may be applied.

Note that it is possible to apply the reproduction of the additional information in the embodiment to a virtual endoscopic image. In the virtual endoscopic image, a moving path of an endoscope is set in the three-dimensional image, and a virtual image similar to an image photographed when the endoscope is caused to move along the moving path in the interior of the human body will be generated by being displayed as a VR image based on the three-dimensional image V0. In the case that the additional information is added under the display condition which is designated to a specific position on the moving path, the additional information will be reproduced in the same manner as the aforementioned embodiment when the display conditions of the virtual endoscopic image fall within the allowable range of the designated display conditions. Here, in the virtual endoscopic image, the position included in the display condition is a three-dimensional position specified by x, y, z coordinates on the three-dimensional image V0. Therefore, the allowable range of e.g., ±10 mm with the three-dimensional position as the reference is set for the position included in the designated display conditions. Further, the direction included in the display condition is the direction viewed from the virtual endoscope on the moving path of the virtual endoscope.

Figure 10:
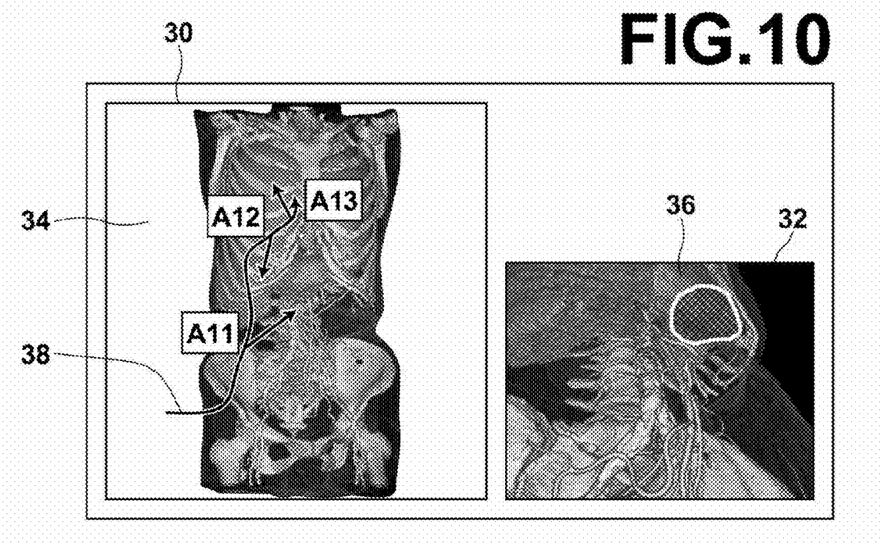
FIG. 10 is a diagram that illustrates an example of display of a VR image and a virtual endoscopic image.

In the virtual endoscopic image, the display unit 28 shows two windows 30, 32 as illustrated in FIG. 10. The window 30 displays a VR image 34 including the entirety of the human body based on the three-dimensional image V0. The window 32 displays a virtual endoscopic image 36. Note that the VR image 34 shows a moving path (camera path) 38 of the endoscope and the directions represented by the display condition for the position and the orientation included in the designated display conditions, which are indicated by arrows. Note that FIG. 10 shows three arrows A11 through A13.

The user changes positions, orientations, enlargement ratios, and color templates while virtually moving the tip of a virtual endoscope along the moving path 38. Through such an operation, the virtual endoscopic image 36 can be displayed in the window 32 with a desired display condition. Further, when the display conditions fall within the range of the designated display conditions, the additional information will be enabled to be reproduced in the virtual endoscopic image 36. Note that in the virtual endoscopic image, the additional information cannot be reproduced when only the position of the display condition falls within the allowable range of the designated display conditions. The additional information will be enabled to be reproduced, when the display conditions of at least both of the position and the orientation fall within the allowable range of the designated display conditions.

Figure 11:
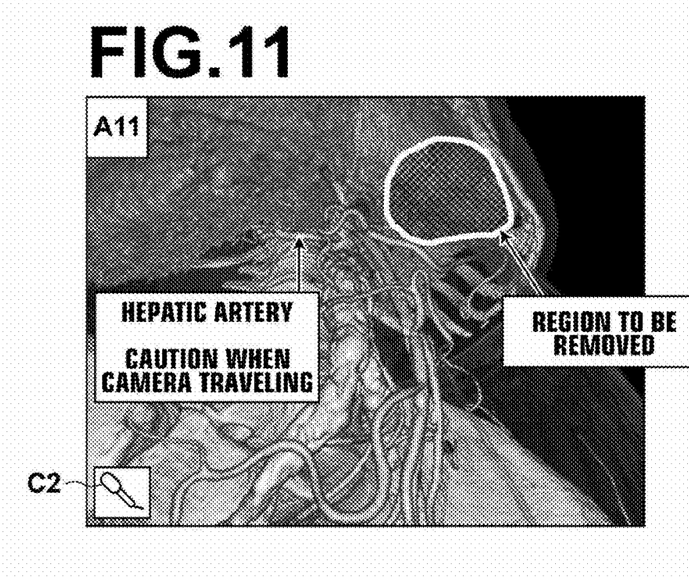
FIG. 11 is a diagram that illustrates an example of the additional information reproduced in the virtual endoscopic image with display conditions indicated by an arrow A11 in FIG. 10.
Figure 12:
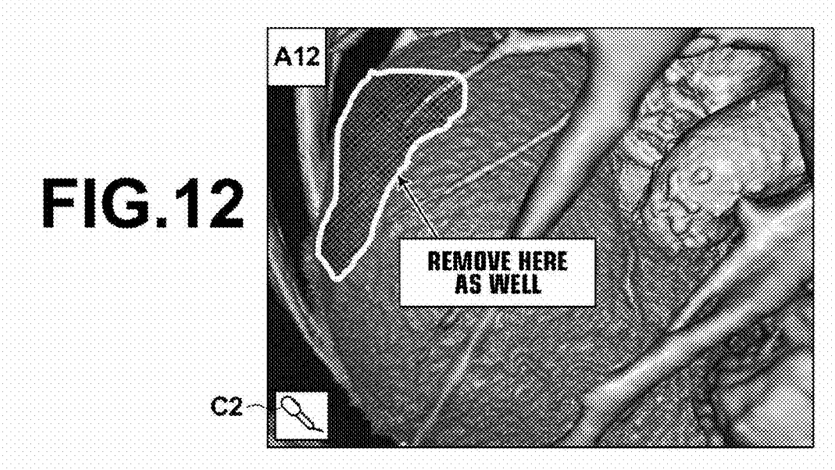
FIG. 12 is a diagram that illustrates an example of the additional information reproduced in the virtual endoscopic image with display conditions indicated by an arrow A12 in FIG. 10.
Figure 13:
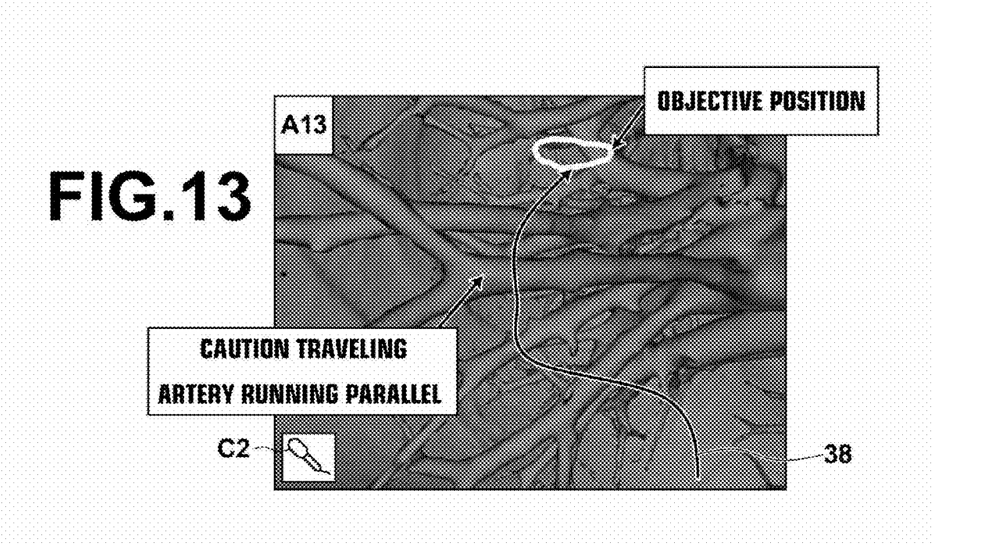
FIG. 13 is a diagram that illustrates an example of the additional information reproduced in the virtual endoscopic image with display conditions indicated by an arrow A13 in FIG. 10.

FIG. 11 shows the example of the additional information which is reproduced in the virtual endoscopic image with the display condition of the arrow A11. FIG. 12 shows the example of the additional information which is reproduced in the virtual endoscopic image with the display condition of the arrow A12. FIG. 13 shows the example of the additional information which is reproduced in the virtual endoscopic image with the display condition of the arrow A13.

The virtual endoscopic image illustrated in FIG. 11 indicates the texts "hepatic artery/Caution: when camera traveling" and "the region to be removed", an object which encloses the region to be cut off, and the icon C2 of the mark of a microphone. The virtual endoscopic image illustrated in FIG. 12 indicates the text "remove here as well" and an object which encloses the region to be removed. The virtual endoscopic image illustrated in FIG. 13 indicates the texts "Caution: traveling/artery running parallel" and "objective position" and a moving path 38 of the endoscope.

As described above, when displaying a virtual endoscopic image, an allowable range is set for each designated display conditions in advance. Further, when the display condition including the orientation falls within the allowable range of the designated display conditions, the additional information correlated with the designated display conditions will be enabled to be reproduced during display of the virtual endoscopic image while changing the display condition. Therefore, only the necessary additional information will be displayed, and unnecessary additional information will not interfere with an observation of the virtual endoscopic image accordingly. Further, it can be easily understood from the reproduced additional information which orientation the virtual endoscopic image has been viewed with, and thereby viewing and understanding the orientation and the additional information of the virtual endoscopic image as a whole are facilitated.

Further, when the display conditions fall within the allowable range of each of the designated display conditions, the additional information is enabled to be reproduced. However, when the VR image is displayed with the arrows A1 through A5, as illustrated in FIG. 3, the following process may be configured to be applied: the user's instructions to select any one of the arrows from the input unit 26 are received first, and then the display condition of the VR image is automatically changed to the designated display conditions as well as the additional information being enabled to be reproduced.

The reproduction of the additional information when the additional information is added to the three-dimensional image of the human body was described in the embodiment mentioned above. It is a matter of course that the present invention can be applied to the case in which additional information is added to a three-dimensional image of the topography data, the case in which additional information is added to a three-dimensional image of cloud in the weather data, or the case in which additional information is added to three-dimensional images of various components in nondestructive inspection.

What is claimed is:

1. A three-dimensional image display apparatus comprising:
    a memory, which stores a plurality of executable instructions; and
    a processor, which executes the stored executable instructions, which when executed by the processor cause the processor to execute the following operations:
        control a display to display a three-dimensional visualization image, the three-dimensional visualization image being obtained by three-dimensionally visualizing a structure of interest extracted from a three-dimensional image;
        setting display conditions including an orientation in which the three-dimensional visualization image of the structure of interest is displayed;
        correlating and storing designated display conditions and additional information, the designated display conditions being designated to add the additional information regarding the three-dimensional visualization image of the structure of interest;
        setting an allowable range for the designated display conditions; and
        determining whether display conditions are within the allowable range of the designated display conditions when displaying the three-dimensional visualization image of the structure of interest while changing the display condition and that enables the additional information correlated with the designated display conditions to be reproduced when an affirmative determination is made,
    wherein, when the additional information is enabled to be reproduced, the processor changes the three-dimensional visualization image of the structure of interest from the display condition to the designated display conditions, and
    wherein the processor further controls the display to display an icon which represents that the additional information present, and further controls the display to display or reproduce the additional information in response to a user manipulating the icon.

2. The three-dimensional image display apparatus of claim 1, wherein the processor sets at least one of a display position, an enlargement ratio, and image quality of the three-dimensional visualization image in addition to the orientation, as the display conditions.

3. The three-dimensional image display apparatus of claim 1, wherein the processor sets at least the orientation and the display position as the display conditions when the three-dimensional image is a virtual endoscopic image.

4. A three-dimensional image display method comprising:
    displaying a three-dimensional visualization image on a display, the three-dimensional visualization image being obtained by three-dimensionally visualizing a structure of interest extracted from a three-dimensional image;
    setting display conditions including an orientation in which the three-dimensional visualization image of the structure of interest is displayed;
    setting an allowable range for designated display conditions designated to add additional information regarding the three-dimensional visualization image of the structure of interest;
    determining whether display conditions are within the allowable range of the designated display conditions when displaying the three-dimensional visualization image of the structure of interest while changing the display conditions; and
    enabling the additional information regarding the three-dimensional visualization image to be reproduced when an affirmative determination is made, the additional information being correlated with the designated display conditions,
    wherein, where the additional information is enabled to be reproduced, the three-dimensionally visualizing step changes the three-dimensional visualization image of the structure of interest from the display condition to the designated display conditions, and
    wherein the three-dimensional image is a volume rendering image which comprises a plurality of structures, and
    wherein the method further comprises displaying an icon which represents that the additional information is present, and displaying or reproducing the additional information in response to a user manipulating the icon.

5. A non-transitory recording medium in which a program for causing a computer to execute a three-dimensional display method has been recorded, comprising the steps of:
    displaying a three-dimensional visualization image on a display, the three-dimensional visualization image being obtained by three-dimensionally visualizing a structure of interest extracted from a three-dimensional image;
    setting display conditions including an orientation in which the three-dimensional visualization image of the structure of interest is displayed;
    setting an allowable range for designated display conditions designated to add additional information regarding the three-dimensional visualization image of the structure of interest;
    determining whether display conditions are within the allowable range of the designated display conditions when displaying the three-dimensional visualization image of the structure of interest while changing the display condition; and
    enabling the additional information regarding the three-dimensional visualization image to be reproduced when an affirmative determination is made, the additional information being correlated with the designated display conditions, wherein, when the additional information is enabled to be reproduced, changing the three-dimensional visualization image of the structure of interest from the display condition to the designated display conditions, wherein the three-dimensional image is a volume rendering image which comprises a plurality of structures, wherein the program further causes the computer to display an icon which represents that the additional information is present and display or reproduce the additional information in response to a user manipulation the icon.

6. The three-dimensional image display apparatus of claim 1, wherein the processor controls the display to display arrows indicating portions to which the additional information is added while a list of the additional information is displayed on a side of the display screen.

* * * * *